United States Patent [19]

Himes et al.

[11] Patent Number: 5,426,208

[45] Date of Patent: * Jun. 20, 1995

[54] METHOD OF PURIFICATION OF ACETONITRILE

[75] Inventors: Barry W. Himes, Guilford; R. Clive Greenough, Milldale, both of Conn.

[73] Assignee: Cryodyne Technologies, Inc., Chester, Conn.

[ * ] Notice: The portion of the term of this patent subsequent to Mar. 8, 2011 has been disclaimed.

[21] Appl. No.: 154,797

[22] Filed: Nov. 19, 1993

Related U.S. Application Data

[63] Continuation-in-part of Ser. No. 64,972, May 21, 1993, Pat. No. 5,292,919, and a continuation-in-part of Ser. No. 886,745, May 21, 1992, abandoned.

[51] Int. Cl.$^6$ ............................................. C07C 253/34
[52] U.S. Cl. ...................................................... 558/435
[58] Field of Search ......................................... 558/435

[56] References Cited

U.S. PATENT DOCUMENTS

| | | | |
|---|---|---|---|
| 2,107,904 | 2/1938 | Pool | 558/435 |
| 2,351,157 | 6/1944 | Semon et al. | 202/42 |
| 3,201,451 | 8/1965 | Idol, Jr. et al. | 558/435 |
| 3,322,814 | 5/1967 | Iappelli | 260/465.1 |
| 3,328,458 | 6/1967 | Iappelli et al. | 260/465.1 |
| 3,870,746 | 3/1975 | Lussling et al. | 558/435 |
| 4,141,826 | 2/1979 | Alford et al. | 210/26 |
| 4,287,345 | 9/1981 | Smiley | 558/435 |
| 4,328,075 | 5/1982 | Fitzgibbons et al. | 558/435 X |
| 4,362,603 | 12/1982 | Presson et al. | 558/435 X |
| 4,430,162 | 2/1984 | Higuchi et al. | 558/435 X |
| 4,474,709 | 10/1984 | Jordan | 558/435 |
| 4,575,434 | 3/1986 | Frank et al. | 558/435 |
| 4,730,215 | 10/1988 | Carlson | 210/722 |
| 5,120,881 | 6/1992 | Rosenfeld et al. | 568/697 |
| 5,156,748 | 10/1992 | Meunier et al. | 210/759 |
| 5,292,919 | 3/1994 | Himes et al. | 558/435 |

FOREIGN PATENT DOCUMENTS

| | | |
|---|---|---|
| 217212 | 9/1985 | Germany . |
| 53-82722 | 7/1978 | Japan . |
| 749828 | 7/1980 | U.S.S.R. . |
| 1318588 | 6/1987 | U.S.S.R. . |

*Primary Examiner*—Joseph Paul Brust
*Attorney, Agent, or Firm*—Curtis, Morris & Safford

[57] ABSTRACT

Acetonitrile is purified by treatment with ozone. After ozone treatment is ended, acetonitrile is passed through packed columns of molecular sieve, activated alumina and charcoal or graphitized carbon; the process results in virtually pure acetonitrile obtained at an efficiency unachievable by prior art processes.

14 Claims, 4 Drawing Sheets

METHOD OF PURIFICATION OF ACETONITRILE

This application is a continuation-in-part of Application Ser. No. 08/064,972, filed on May 21, 1993, which is now U.S. Pat. No. 5,292,919 granted Mar. 8, 1994 and which in turn is a continuation-in-part of Application 07/886,745, filed May 21, 1992, allowed but now abandoned.

This invention relates to a process for the purification of chemicals and in particular to the improved purification of acetonitrile. According to this improved process, acetonitrile is purified without using expensive equipment or corrosive chemicals such as amines with substantially no waste of the desired product, except the impurities. Prior art methods for the purification of acetonitrile involve at least one stage of distillation. A distillation stage is both costly and inefficient and the overall waste product is about 25% of the starting material. Using the present invention, acetonitrile purification is accomplished at great product savings, more efficiently; and, moreover, without the use of a distillation stage(s).

BACKGROUND OF THE INVENTION

Acetonitrile must be of an exceptionally high purity for use in UV spectrophotometry, electroanalytical studies, lithium-sulfur batteries, high performance liquid chromatography and DNA synthesis. In particular, acetonitrile must be exceptionally pure for these uses with regard to such as UV absorbing materials and water. Prior art methods of purifying acetonitrile have been unsatisfactory for a variety of reasons. One reason is that the methods generally involve at least one stage of distillation. A distillation stage is both costly in capital and operating costs and inefficient due to high losses e.g. in the bottoms of the stills if usual oxidation methods are used. The process of purification of the present invention does not use a single distillation stage yet achieves exceptional purity of low water content in the product, great capital savings at substantially no impact on environment because of substantially no wastes, and at great energy savings.

There are many other disadvantages of the prior art methods which are overcome by the present invention. For example, the process of the present invention does not use corrosive chemicals such as amines or environmentally detrimental compounds such as permanganates, and the purity of the acetonitrile which is achieved is somewhat higher according to the process of this invention than with any prior art methods known to the inventors. The product is substantially impurity "finger print" free and is achieved without the asymptotically raising costs (and effort) associated with the prior art required to achieve the same purity level.

One source of acetonitrile is from the production of acrylonitrile by gas phase oxidation of propylene and ammonia with oxygen. Acetonitrile is a by-product of the production of acrylonitrile, and as such may be highly impure depending, for example, upon the mode of operation of the acrylonitrile plant and the method of clean-up for the by-product acetonitrile. Typical of the impurities associated with acetonitrile include at least one or more of the following: oxazole, acrylonitrile, crotonitrile, methacrylonitrile and perhaps methyloxazole. Water is also present in acetonitrile. Additional impurities are also likely to be present, again depending on the process conditions experienced in the production of acrylonitrile, the source of acrylonitrile and the partial purification steps attempted. One of the undesirable class of impurities are aromatic compounds and for sake of greater efficiency this invention also relates to the removal of aromatic impurities from acetonitrile.

A number of prior attempts to purify acetonitrile have been carried out but have not been satisfactory as noted above. The potential or ultimate amount and quality of purified acetonitrile which can be recovered is a goal against which all attempts have been measured. This ultimate goal has eluded many attempts, especially on an industrial scale.

THE PRIOR ART

A considerable somewhat related effort has been devoted to the purification of various chemicals.

For example, U.S. Pat. No. 2,107,904 disclosed adsorbents for adsorbing aliphatic nitriles from liquid mixtures in hydrocarbons. The adsorbents include alumina.

U.S. Pat. No. 2,560,931 discloses the dehydration of acetonitrile by treating it with activated alumina.

U.S. Pat. No. 2,660,559 discloses a process whereby ozone is used for various processes including the purification of liquids. In one process disclosed, ozone is generated, mixed with the gas or liquid (including water) to be purified, and the undesirable material or organic matter is removed.

U.S. Pat. No. 2,807,573 disclosed the separation and purification of acrylonitrile from mixtures containing acetonitrile by subjecting the mixtures to an extractive distillation employing water as the solvent.

U.S. Pat. No. 3,372,163 disclosed treating a liquid with ozone. The liquid is defined in column 3 as any liquid with components which are susceptible to ozone oxidation.

U.S. Pat. No. 3,920,547 discloses a method for the destruction of cyanides in an aqueous cyanide solution, by contacting the solution with an ozone-containing gas while simultaneously irradiating the aqueous solution with UV light.

U.S. Pat. No. 4,059,492 discloses the purification of waste water from acrylonitrile production with steam, optionally in the presence of an organic amine.

U.S. Pat. No. 4,341,641 discloses a process for treating cyanide and cyanate containing waste waters with ozone containing gas to substantially destroy the cyanide content therein.

DL 0217212 discloses purification of acetonitrile by treatment with ozone and distillation.

DL 0225692 discloses purification of acetonitrile by oxidation.

Finally, DL 0229274 discloses acetonitrile purified by (i) catalytic oxidation with oxygen or gas containing at least one volume percent of oxygen; (ii) post oxidation treatment with a solid inorganic compound; and (iii) rectification, i.e., distillation.

However, none of these references teaches or suggests the combination process disclosed herein with the associated product savings, elimination of waste disposal problems, energy savings, etc. Moreover, none of the references discloses the high purity achieved by a process as simple as the process of this invention. For example, the process described in DL 0217212 required distillation after ozonization, and the reduction in impurities is not allocated to each step. The final product still is not spectroscopically pure by any reasonable definition. The final product contains, for example, 25 ppm of oxazole. The process of the present invention, on the other hand, strips all the impurities originally present down to non-detectability (i.e., less than 0.2 ppm of each indicated impurity) and shows an essentially impurity "finger print" free product.

BRIEF DESCRIPTION OF THE INVENTION AND DRAWINGS

It has now been discovered that an improved process for the purification of acetonitrile may be practiced with great success. Thus, increased yields of highly purified acetonitrile have been achieved simply and economically, and other prior art shortcomings have been minimized.

The present method first removes water to a desired limit from the product, i.e. from about 500 ppm to about 5 ppm, and uses ozone to oxidize all the deleterious impurities of acetonitrile. After ozone treatment is ended, the acetonitrile is passed through packed columns of a molecular sieve, activated alumina and charcoal or graphitized carbon. All of the oxidation products, water and any excess ozone are stripped from the desired product by this process. The process results in virtually pure acetonitrile (with substantially non-detectable impurity levels).

With reference to the Figures herein:

DETAILED DESCRIPTION OF THE INVENTION

Figure 1:
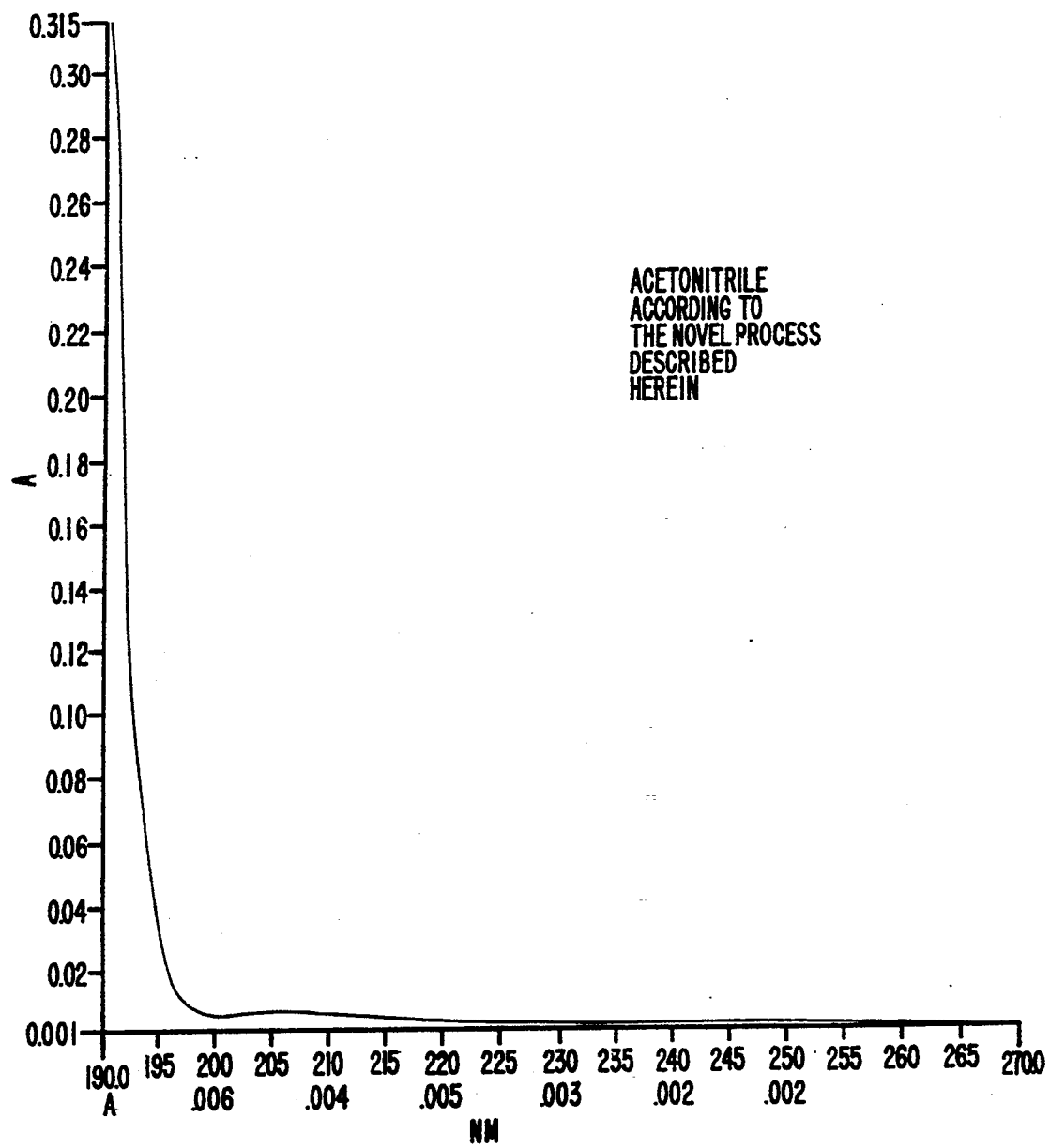
FIG. 1 illustrates the purity of acetonitrile obtained according to the novel process described herein.

As previously indicated, acetonitrile must be of exceptionally high purity for use in UV spectrophotometry, electroanalytical studies, DNA chemistry and high performance liquid chromatography. Prior art methods of purifying acetonitrile have been unsatisfactory for a variety of reasons. It has now been discovered that an improved process for the purification of acetonitrile may be practiced. Thus, primarily increased yields of highly purified acetonitrile have been achieved simply and economically, and other prior art shortcomings have been minimized. For example, product yields have been improved by eliminating most of the 25% loss experienced by the best prior art methods based on distillation steps used by the prior art. Energy use has been decreased about two to about three fold when compared to the best prior art methods including distillation steps known to the inventors.

Typically today, acetonitrile is obtained as a by-product of the production of acrylonitrile by gas phase oxidation of propylene and ammonia with oxygen. Whether it is obtained as such by-product or as a product from another source, acetonitrile is highly impure. Typical impurities associated with acetonitrile include one or more of the following: water, oxazole, acrylonitrile, crotonitrile, acetamide, methacrylonitrile and perhaps methyloxazole. All of the impurities may be present or some may be absent such as oxazole, methyloxazole or sometimes methacrylonitrile. Additional impurities are also likely to be present. The present process may start with impurity levels as low as 10 ppm of any combination of the above impurities and reduce the total level to less than detectable levels. A detectable level of impurities is about 0.2 ppm. For the most part, additional impurities are a function of the process conditions and associated variables. Nevertheless, these additional impurities do not cause the present process to lose its effectiveness as the process is able to address effectively all heretofore encountered, undesired impurities. It has been further found that because aromatic impurities are more difficult to remove, time-requirement wise, by ozone oxidation, a combination of activated charcoal removal of aromatic compounds still further improves the process as now ozonation requires only about half the time to remove the further impurities after the impure acetonitrile has been treated with activated charcoal. Such treatment with activated charcoal may be used, as appropriate, in the process sequence.

As mentioned above, a number of prior attempts to purify acetonitrile have been carried out, but have not been satisfactory because while these could reduce the impurities to very low limits, these reductions could not be achieved by any practical, industrially efficient process. The improved process for the purification of acetonitrile of the present invention achieves the goal by an industrially efficient, fast and substantially waste-free process that has eluded the prior art and is now achieved by use of ozone (in combination and as a prerequisite part of other steps) in fine bubble form to oxidize all the deleterious impurities of acetonitrile. After ozone treatment has ended, the acetonitrile is passed through packed columns of a) a molecular sieve, b) activated alumina and c) charcoal or graphitized carbon. All of the oxidation products, water, and any excess ozone are stripped out by this process.

The source of the ozone used in the process according to the invention is of no particular importance. One source is from an ozone generator whose feed is oxygen or an oxygen-nitrogen mixture. The gas is passed through a corona discharge reactor. The discharge flow is typically set at from 1 to 7 cu ft/min, and the generator voltage is set, typically to give from 0.1 to 3 percent ozone, preferably up to about 3 percent ozone. The output gas is then diluted by 50 percent with nitrogen, utilizing linear mass flow controllers to yield a $\leq 15\%$ oxygen content.

This ozone mixture is then passed through the acetonitrile by any conventional means. For example, the ozone discharge mixture can be passed through the acetonitrile by means of a sparging frit producing a fine bubble size. The time needed to oxidize all of the deleterious impurities is dependent upon the initial ozone concentration, the efficiency of ozone transfer to the acetonitrile and the level and nature of the impurities in the acetonitrile, the latter being the most variable (about 10–500 ppm for usual commercial acetonitrile). Now with charcoal removal of aromatic compounds, the process is further improved. By aromatic compounds we mean single ring cyclic compounds with multitude of hydrocarbon and other substituents as well as polycyclic aromatic compounds with similar substituents.

In a typical process confirming the effectiveness of this invention, a 6000 gallon batch of acetonitrile is purified. The ozone discharge mixture usually ranges from about 0.1 to 1.5 percent ozone, preferably about 1 percent ozone. Accordingly, the time for the oxidation step in a typical 6000 gallon batch ranges from about 15 to 750 minutes for about 10 to 500 ppm impurity starting material. Generally, about 60 minutes are required to purify a 6000 gallon batch of acetonitrile using 1 percent ozone. The contents of the reactor are monitored by taking samples at intervals (half-hour) and analyzing for the deleterious impurities by high performance liquid chromatography with a column and material as identified in FIG. 3.

To remove the dissolved ozone, if desired, the ozone generator is turned off. During this time a nitrogen gas flow is continued for several minutes, typically 10 to 60 minutes to sparge and strip the liquid of any residual ozone.

After the ozone treatment is ended and the dissolved ozone has been removed, the acetonitrile is passed through a packed column of an activated molecular sieve, activated alumina and charcoal or graphitized carbon. The typical conditions under which the acetonitrile passes through the packed columns are ambient temperature and 3 gal/min flow. Flow rates from 2 to 6 gal/min are readily achievable.

All of the nonvolatile oxidation products, water and excess ozone, if any is still remaining, are stripped out by this step of the process. To verify the purity of the acetonitrile, the acetonitrile can be checked for UV absorbance by scanning the material with a spectrophotometer in the range of from about 270 to 190 nm. The result shows a highly purified acetonitrile, with water content of 4.3 ppm as determined by coulometric KF titrator.

The following example illustrates the process of the invention and some of its improvements as disclosed herein with respect to the purification of acetonitrile. The acetonitrile utilized in the examples are from BP Chemicals taken from its Lima, Ohio plant. As received, the crude acetonitrile already has been upgraded to contain less than 100 ppm of all UV-absorbing impurities.

EXAMPLE 1

A comparative series of tests were done directly comparing the purification of acetonitrile with ozone, followed by distillation to purification of acetonitrile with ozone followed by passing the product through a packed column of activated alumina. The results are as follows:

1. Ozone plus activated alumina The ozone treatment was performed as follows:

An ozone generator was used with an oxygen-nitrogen mixture comprising 20 percent oxygen and 80 percent nitrogen as feed. The oxygen-nitrogen mixture was passed through the corona discharge reactor. The flow was set at 7 cu ft/min and the generator voltage was set to give approximately 2 percent ozone and that mixture was diluted with 7 cu ft/min of nitrogen.

It has also been found advantageous to precool, after ozonation, the crude acetonitrile being treated to less than 20° C. and to maintain the column at less than 20°0 C. Although it seems innocuous, pre-cooling allows the material being treated conventionally to be improved by removing at the front end, the various "front end" impurities. "Front end" impurities are those impurities which are stripped from the column at an early stage because of the exothermic heat content of the reaction. Removal of "front end" impurities also minimizes the overall content of the impurities and thus causes product, especially at the beginning of the reaction to be very pure.

The resulting ozone mixture was passed for 60 minutes through 6000 gallons of acetonitrile containing 20 ppm of impurities by means of a sparging frit.

After ozonization, the generator was turned off and nitrogen gas alone was sparged through the system for 30 minutes. The high performance liquid chromatography (HLPC) analysis showed no peaks of the previously present impurities but there are large amounts of oxidation products.

6000 gallons of acetonitrile was then passed through packed columns of 3Å to 10Å molecular sieves, preferably the smaller. The purity of the product after this step showed no substantial changes according to UV or HPLC analysis but the water content was reduced from 300 to 4.3 ppm. Thereafter, the thus treated product of the preceding purity was passed through a packed column of activated alumina. HPLC analysis showed no peaks at all. A charcoal or graphitized carbon column was then used for the thus far purified materials. For the above steps the conditions were as follows:

flow—about 3 gal/min
temperature—at about ambient conditions

The final purity of the product was checked for UV absorbance by scanning from 270 to 190 nm with a spectrophotometer. The results appear in the table below. The total loss of product was less than 0.065% versus about 15 to 25% based on the best prior art distillation methods. The purity of the product after this step was:

TABLE I

| Sample 1 | |
| --- | --- |
| Wavelength (nm) | Absorbance |
| 200 | .006 |
| 210 | .007 |
| 220 | .005 |
| 250 | .002 |

The absorbencies at 200, 210 and 220 nm measure the effectiveness of the removal of the oxidation products, i.e., acetamide. The lower the values the less error exists in its use. The best prior art process, of a typical purified sample obtained from J. T. Baker of Phillipsburg, N.J., gave the following readings as shown in Table II below:

TABLE II

| Wavelength (nm) | Absorbance |
| --- | --- |
| 200 | .019 |
| 210 | .017 |
| 220 | .011 |
| 250 | .0015 |

If after ozone treatment only packed columns of alumina and charcoal or graphitized carbon were used, then the purity level was the same as with the complete set of columns.

Figure 2:
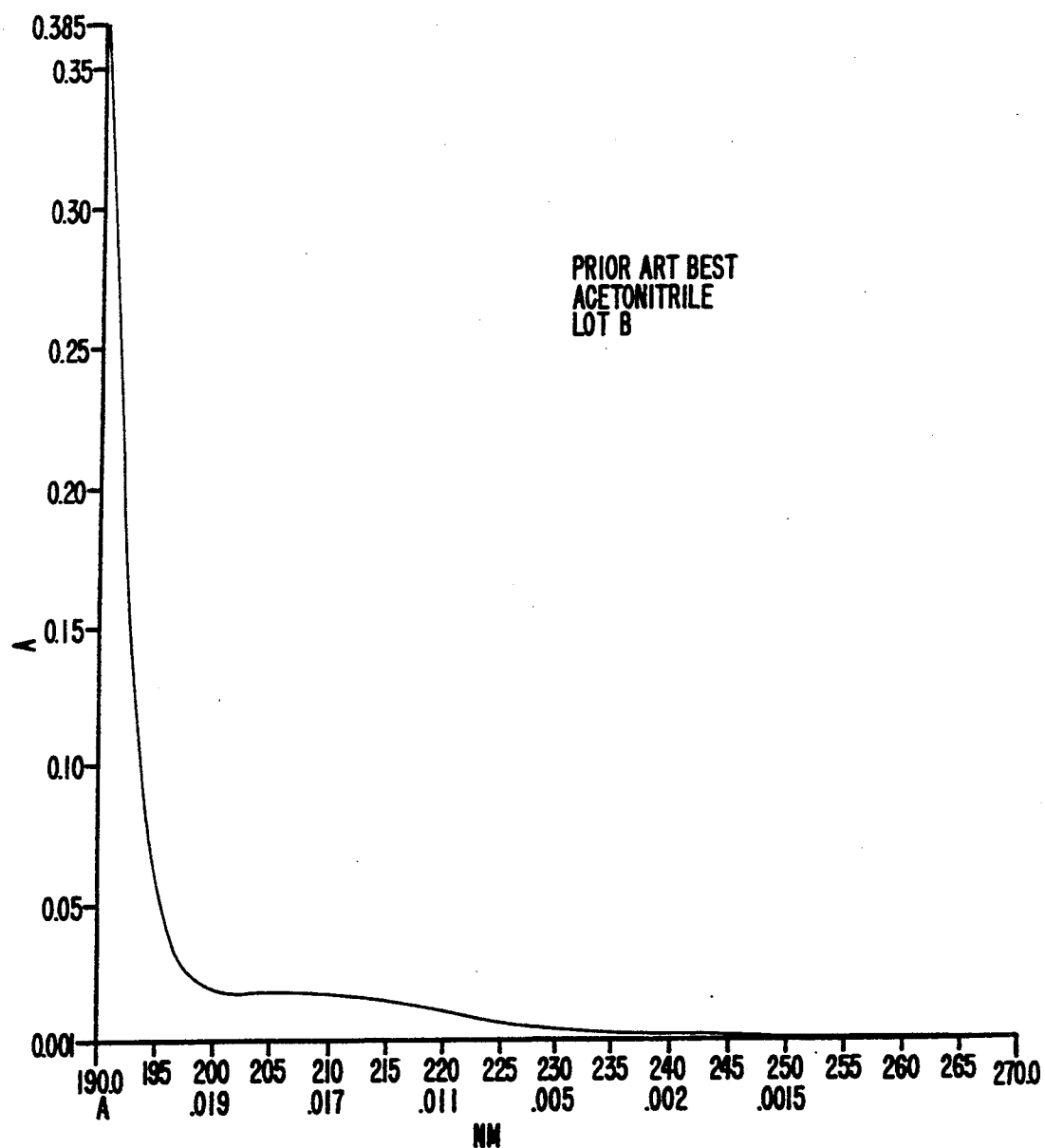
FIG. 2 illustrates the purity according to the best prior art process known which requires extensive distillation and waste of product.
Figure 3:
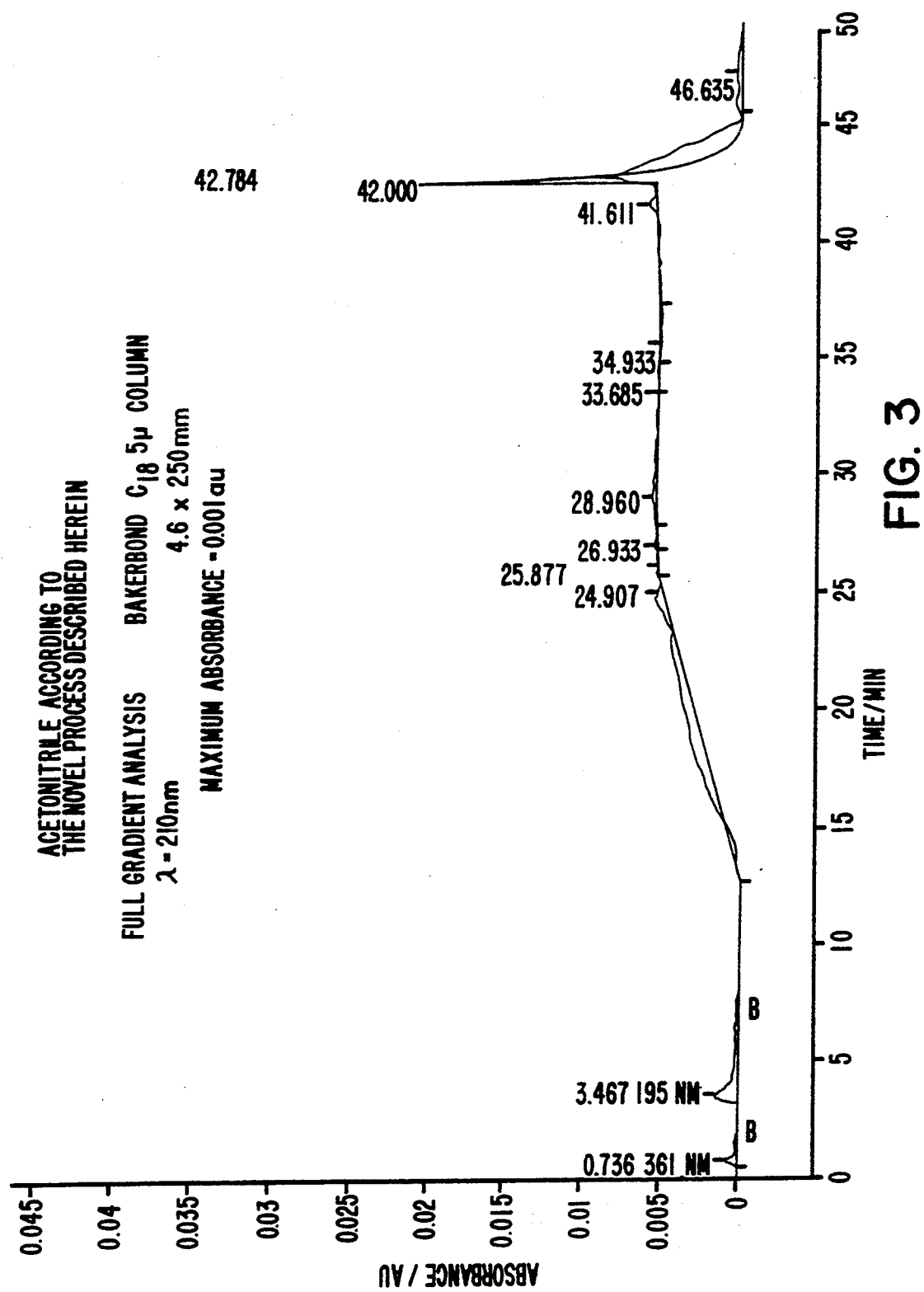
FIG. 3 illustrates acetonitrile obtained according to the novel process described herein with the column material being "Bakerbond" $c18$ 5 $\mu$ with a column size of 4.6×250 mm.
Figure 4:
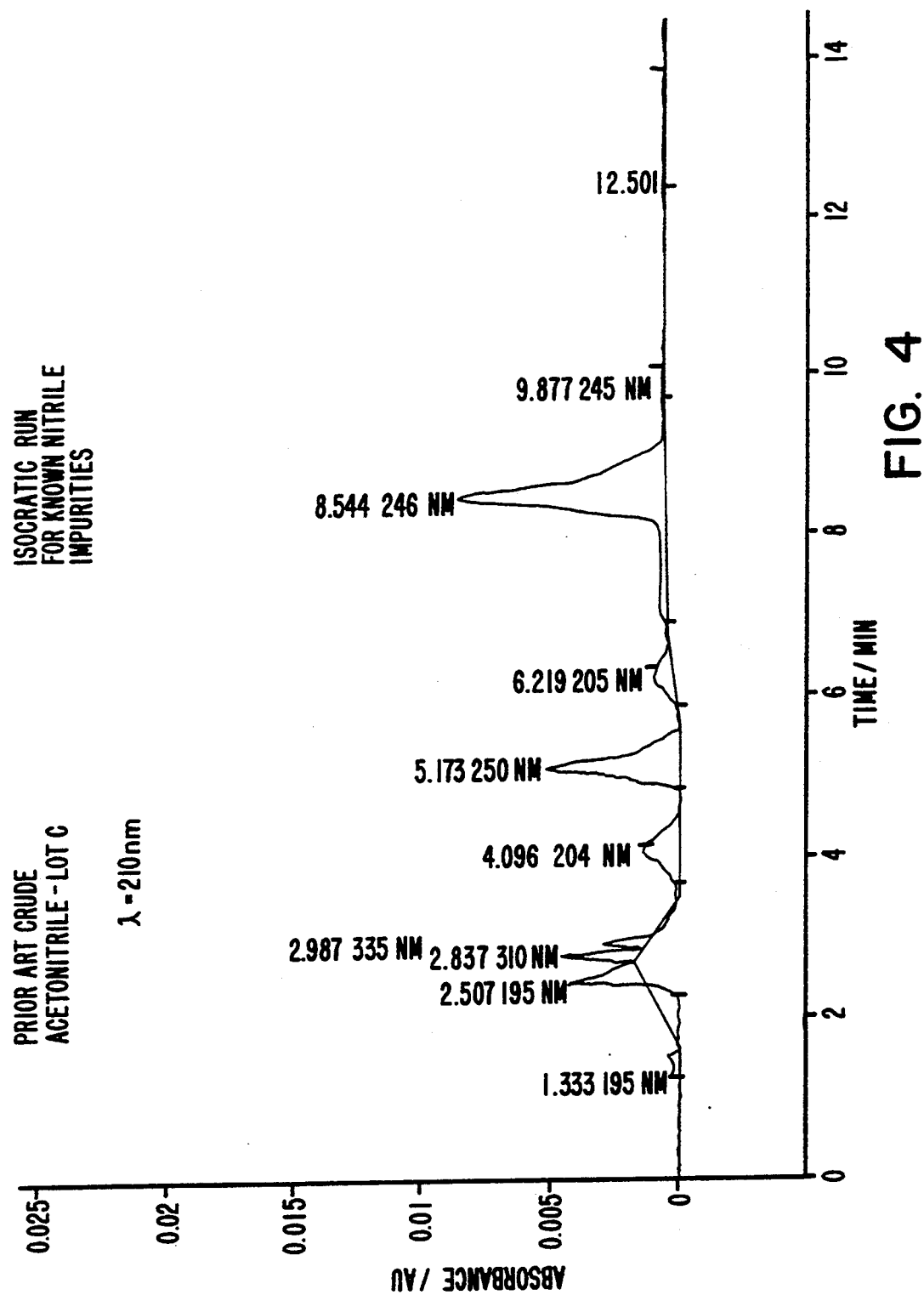
FIG. 4 identifies the typical impurities from a prior art starting material acetonitrile.

The FIGS. 1 and 2 herein show two curves: in FIG. 1 according to the present invention and in FIG. 2 according to the best prior art sample. FIG. 3 is a high performance liquid chromatography gradient run which concentrates the impurities from a very large sample loaded over a 10 minute period. For comparison, FIG. 4 is a run on the same equipment which identifies the impurities for a prior art (lot C) acetonitrile.

The present process is generally starting material source independent, does not require use of potassium permanganate for oxidation (permanganate disposal is very undesirable from an environmental standpoint).

Molecular sieves are generally of the 3A to 10A size and are readily available from sources such as Mobil Oil of McLean, Virginia or Union Carbide of Danbury, Conn. Alumina is used as grains of 12-28 mesh size. Other shapes are also employable. Other advantageous materials are zirconia and silica used in about the same size as alumina.

Silica gel is available from W. R. Grace of Baltimore, Md., and zirconia from Norton Co. of Worcester, Ma.

As carbon, graphitized carbon, charcoal and similar aromatic compound free carbon sources may be employed. Carbon of such type is readily available from Westvaco of Covington, Va. for charcoal; graphitized carbon is available from Rohm and Haas of Philadelphia, Pa.

Typically, carbon in a bed is of 12 to 20 mesh size.

Specification sheets such as OSHA data sheets, are readily available from the above organizations for the above mentioned products.

The foregoing example is considered to be representative of the principles of the instant invention, but is given here as an illustration only and should not be interpreted as limiting the scope of the invention. Obviously, many modifications which fall within the scope of the invention will be apparent to those skilled in the art.

We claim:

1. A combination method for removal of deleterious impurities from acetonitrile of a total starting impurity amount of above 10 ppm wherein the deleterious impurities are water and at least one or more of the following: oxazole, acrylonitrile, crotonitrile, acetamide, methacrylonitrile, and methyloxazole, comprising: treating at ambient temperature acetonitrile with ozone for a time sufficient to oxidize the deleterious impurities in said acetonitrile; and, then passing the thus ozone treated acetonitrile through columns of at least a), and b) or a), b) and c) and wherein a) is a molecular sieve; b) is activated alumina, zirconia or silica gel and c) is charcoal or graphitized carbon, whereby a substantially impurity free acetonitrile is obtained wherein each of the deleterious impurities present are substantially entirely removed as determined spectrographically.

2. The method as defined in claim 1, wherein the deleterious impurities are at least acrylonitrile, crotonitrile, and acetamide.

3. The method as defined in claim 1, wherein the deleterious impurities are at least acrylonitrile, crotonitrile, acetamide and methacrylonitrile.

4. The method as defined in claim 1, wherein the deleterious impurities are at least 10 ppm.

5. The method as defined in claim 1, wherein after the acetonitrile is treated with ozone in bubble form, the ozone is removed from said acetonitrile by stripping ozone with nitrogen.

6. The method as defined by claim 5, wherein the acetonitrile is stripped with nitrogen for at least 2 minutes.

7. The method as defined in claim 1, wherein the ozone is up to about 2.0 percent ozone.

8. The method as defined in claim 6, wherein the ozone is 1.0 percent ozone.

9. The method as defined in claim 1, wherein the ozone treatment lasts for approximately 60 minutes.

10. The method as defined in claim 1, wherein acetonitrile is scanned spectrographically to determine acetonitrile purity in a range from about 190 nm to 270 nm to determine deleterious impurities present after said acetonitrile has passed through packed columns of a) and b) and said acetonitrile purity is compared with a starting material for establishing completeness of purification.

11. The method as defined in claim 10, wherein the packed column b) zirconia is used.

12. The method as defined in claim 1, wherein at least packed columns of a) and b) are used in conjunction with ozone treatment.

13. The method as defined in claim 1, wherein at least packed columns of b) is used in conjunction with ozone treatment for a period of up to about 750 minutes.

14. The method as defined in claim 1, wherein at least packed columns of b) and c) are used in conjunction with ozone treatment.

* * * * *